US010322237B2

(12) United States Patent
    Fabien (10) Patent No.: US 10,322,237 B2
(45) Date of Patent: Jun. 18, 2019

(54) AUTOINJECTOR

(71) Applicant: APTAR FRANCE SAS, Le Neubourg (FR)

(72) Inventor: David Fabien, Plouarzel (FR)

(73) Assignee: APTAR FRANCE SAS, Le Neubourg (FR)

( * ) Notice: Subject to any disclaimer, the term of this patent is extended or adjusted under 35 U.S.C. 154(b) by 3 days.

(21) Appl. No.: 15/323,560

(22) PCT Filed: Jul. 2, 2015

(86) PCT No.: PCT/FR2015/051833
    § 371 (c)(1),
    (2) Date: Jan. 3, 2017

(87) PCT Pub. No.: WO2016/001595
    PCT Pub. Date: Jan. 7, 2016

(65) Prior Publication Data
    US 2017/0165426 A1    Jun. 15, 2017

(30) Foreign Application Priority Data

Jul. 4, 2014    (FR) ..................................... 14 56445

(51) Int. Cl.
    *A61M 5/20*    (2006.01)
    *A61M 5/32*    (2006.01)
    (Continued)

(52) U.S. Cl.
    CPC ........ *A61M 5/2033* (2013.01); *A61M 5/3158* (2013.01); *A61M 5/31515* (2013.01);
    (Continued)

(58) Field of Classification Search
    CPC .......... A61M 5/2033; A61M 2005/206; A61M 2005/2013; A61M 5/3202; A61M 5/326;
    (Continued)

(56) References Cited

U.S. PATENT DOCUMENTS 3,941,130 A * 3/1976 Tibbs .................. A61M 5/2033
                                                    604/136
4,465,478 A * 8/1984 Sabelman ............. A61M 5/315
                                                    604/224
(Continued)

FOREIGN PATENT DOCUMENTS

EP    2 705 862 A1    3/2014
FR    2 654 938 A1    5/1991
                (Continued)

OTHER PUBLICATIONS

International Preliminary Report on Patentability dated Jan. 19, 2017 from the International Bureau and Written Opinion from the International Searching Authority in counterpart International Application No. PCT/FR2015/051833.
(Continued)

*Primary Examiner* — Scott J Medway
(74) *Attorney, Agent, or Firm* — Sughrue Mion, PLLC (57) ABSTRACT

An autoinjector having a reservoir containing fluid and including: a piston; a piston rod cooperating with the piston and is movable between a rest position and an injection position in which the piston rod has moved the piston to inject the fluid; an actuator spring urging the piston rod towards its injection position; a force-adjustment system exerting at least one force on the piston rod, the force adding to the force exerted by the spring on the piston rod at the beginning of injection; two pivot members cooperating with the piston rod and are connected together by two resilient elements, at least one pivot member being blocked prior to actuation by a locking system, thus preventing the autoinjector from being actuated, and an unlocking element adapted to move and/or to deform the locking system so as to unblock the at least one pivot member.

15 Claims, 6 Drawing Sheets

(51) Int. Cl.
*A61M 5/315* (2006.01)
*A61M 5/46* (2006.01)

(52) U.S. Cl.
CPC .............. *A61M 5/326* (2013.01); *A61M 5/46* (2013.01); *A61M 2005/206* (2013.01); *A61M 2005/208* (2013.01); *A61M 2005/2086* (2013.01); *A61M 2205/581* (2013.01)

(58) Field of Classification Search
CPC .. A61M 2005/2073; A61M 5/24; A61M 5/20; A61M 2005/208; A61M 5/28
See application file for complete search history.

(56) References Cited

U.S. PATENT DOCUMENTS

| | | | |
|---|---|---|---|
| 4,787,893 A * | 11/1988 | Villette | A61C 19/08 433/118 |
| 5,137,516 A | 8/1992 | Rand et al. | |
| 5,267,963 A * | 12/1993 | Bachynsky | A61F 5/41 604/134 |
| 5,865,804 A * | 2/1999 | Bachynsky | A61M 5/2033 604/131 |
| 8,308,687 B2 * | 11/2012 | Carrel | A61M 5/326 604/136 |
| 8,888,804 B2 * | 11/2014 | Schraga | A61B 5/1411 606/181 |
| 2001/0005781 A1 * | 6/2001 | Bergens | A61M 5/2033 604/208 |
| 2002/0077601 A1 * | 6/2002 | Kawagishi | A61M 5/20 604/224 |
| 2002/0095120 A1 * | 7/2002 | Larsen | A61M 5/2033 604/187 |
| 2008/0195056 A1 * | 8/2008 | Bishop | A61M 5/2033 604/218 |
| 2012/0088206 A1 * | 4/2012 | Tanaka | A61M 5/20 433/90 |
| 2016/0175534 A1 | 6/2016 | Fabien | |

FOREIGN PATENT DOCUMENTS

| | | | | |
|---|---|---|---|---|
| WO | 2009/010591 A2 | 1/2009 | | |
| WO | 2011/101382 A1 | 8/2011 | | |
| WO | WO2012045838 A1 * | 4/2012 | ............. | A61M 5/20 |
| WO | 2015/001280 A1 | 1/2015 | | |

OTHER PUBLICATIONS

International Search Report for PCT/FR2015/051833, dated Oct. 26, 2015.

* cited by examiner

AUTOINJECTOR

CROSS REFERENCE TO RELATED APPLICATIONS

This is a National Stage of International Application No. PCT/JP2015/051833 filed Jul. 2, 2015, claiming priority based on French Patent Application No. 1456445 filed Jul. 4, 2014, the contents of all of which are incorporated herein by reference in their entirety.

BACKGROUND OF THE INVENTION

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they all present a certain number of drawbacks.

Thus, for autoinjectors that use the same spring both for initial pricking then for injection proper, the spring must be sufficiently strong to guarantee the injection stage in full. This is particularly true given that a relatively large force is generally required at the beginning of the injection stage, in order to start the movement of the piston of the syringe. As a result, the spring delivers its maximum power during pricking, which may make the pricking stage painful. Furthermore, with such a spring that is very powerful during pricking, there exists a significant risk of breaking the collar of the syringe, in particular when it is a glass syringe.

In addition, it is desirable to avoid any risk of the autoinjector being triggered accidentally, e.g. during storage or transport, without however making the device too complex or too difficult to actuate.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable and safe in use, that makes it possible to guarantee that all of the fluid is dispensed to the desired location, and that is simple and inexpensive to manufacture and to assemble.

SUMMARY OF THE INVENTION

The present invention thus provides an autoinjector comprising a body, and a reservoir containing fluid and including a piston and a needle, such as a pre-filled syringe, said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force F2 on said piston rod, said force F2 adding to the force exerted by said actuator spring on said piston rod at the beginning of injection, so as to amplify the force exerted on said piston by said piston rod at the beginning of injection, said force-adjustment system comprising two pivot members that co-operate with said piston rod, said pivot members being connected together by two resilient elements, at least one pivot member being blocked prior to actuation by a locking system, thus preventing the autoinjector from being actuated, said autoinjector further comprising an unlocking element that is adapted to move and/or to deform said locking system so as to unblock said at least one pivot member, and thus make it possible to actuate the autoinjector.

Advantageously, said body includes a sleeve, said pivot members being mounted to pivot on said sleeve about pivot pins that are parallel.

Advantageously, said resilient elements are fastened to said pivot members via parallel movable pins, such as rods having two side edges, that are formed on said pivot members.

Advantageously, when the piston rod moves towards its injection position, said movable pins are arranged behind said stationary pins in the travel direction of said piston rod, said loaded resilient elements, at the beginning of travel of the piston rod towards its injection position, causing said pivot members to pivot in such a manner as to relax said resilient elements, thereby creating an amplification force F2 at the beginning of injection.

Advantageously, each pivot member includes a plurality of projections that are adapted to co-operate with a plurality of radial projections of the piston rod.

Advantageously, said autoinjector is actuated by an axial button.

Advantageously, prior to injection, said piston rod is initially moved by said actuator spring between said rest position and a pricking position in which said piston rod has moved said reservoir relative to said body so as to perform pricking.

Advantageously, during pricking, the piston rod co-operates with the piston of the reservoir so as to move said reservoir relative to the body.

Advantageously, when the piston rod moves from its rest position towards its pricking position, said movable pins are arranged in front of said stationary pins in the travel direction of said piston rod, said piston rod, at the end of travel towards its pricking position, causing said pivot members to pivot so as to load said resilient elements, thereby creating a braking force F1 at the end of pricking, said force F1 being opposed, at the end of pricking, to the force exerted by said actuator spring on said piston rod, so as to decrease the force exerted on said reservoir by said piston rod at the end of pricking.

Advantageously, said locking system includes at least one locking element that is movable and/or deformable between a locked position in which it prevents at least one pivot member from pivoting, and an unlocked position in which said at least one pivot member can pivot.

Advantageously, said at least one locking element is urged resiliently towards its locked position by a drive member, such as a resilient blade.

Advantageously, said at least one locking element is mounted to pivot on a sleeve of said body, about a pivot pin.

Advantageously, said at least one locking element comprises a blocking portion that co-operates directly with a pivot member, and a control portion that co-operates with said unlocking element.

Advantageously, said unlocking element is formed on an actuator sleeve that is slidably mounted in said body, and that has an axial end surface that is in contact with the zone in which injection is to take place, said actuator sleeve being adapted to slide relative to said lower body between an initial rest position in which it projects axially out from said lower body prior to actuation, an actuated position in which it is moved axially towards the inside of said lower body, and a final safety position in which it once again projects out from said lower body, so as to cover the needle of the syringe after injection, said actuator sleeve being urged axially towards the outside of said lower body by a spring.

Advantageously, said unlocking element co-operates with said locking system at the end of stroke of said actuator sleeve, between its initial rest position and its actuated position, in particular when said actuator sleeve has performed at least 90% of said stroke.

BRIEF DESCRIPTION OF THE DRAWINGS

These characteristics and advantages and others of the present invention appear more clearly from the following detailed description, given by way of non-limiting examples, and with reference to the accompanying drawings, and in which.

DESCRIPTION OF THE PREFERRED EMBODIMENTS

The autoinjector is described below with reference to two advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

Figure 1:
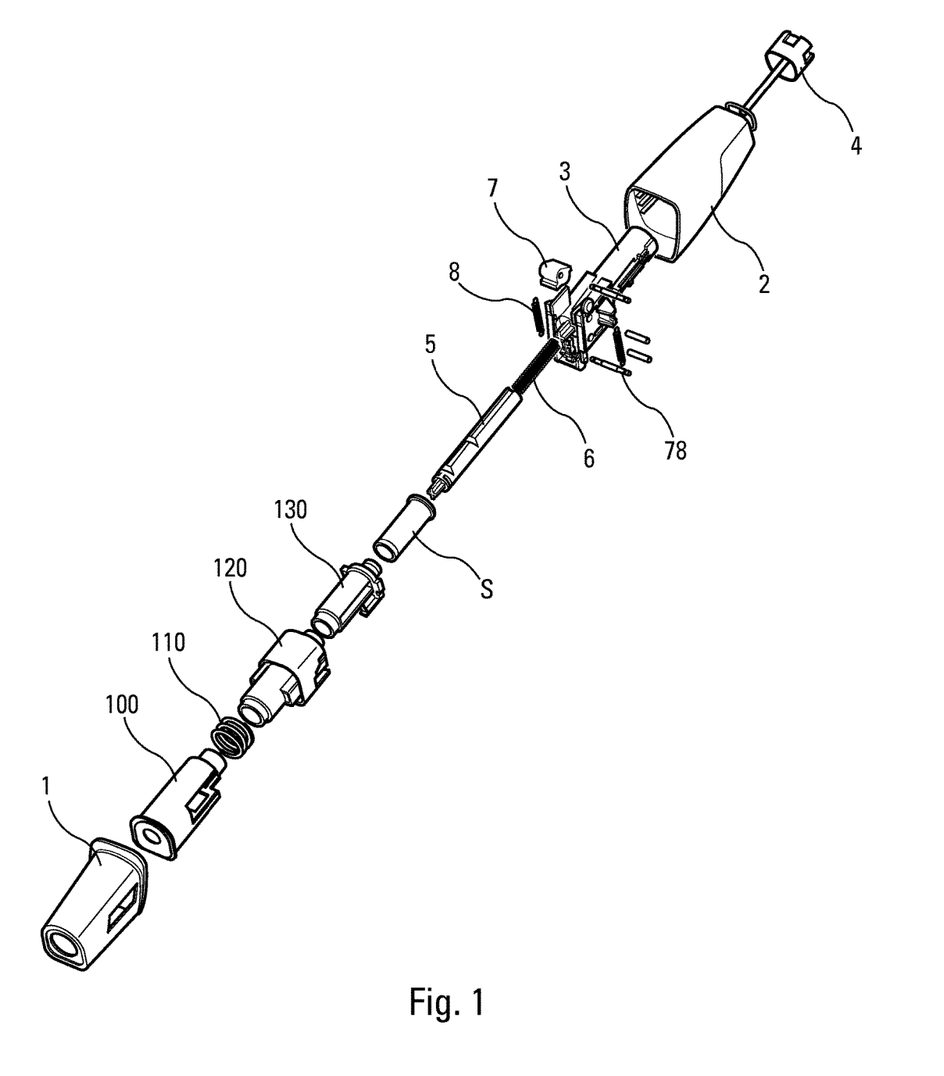
FIG. 1 is an exploded diagrammatic perspective view of the components of an autoinjector, in an advantageous embodiment.
Figure 2:
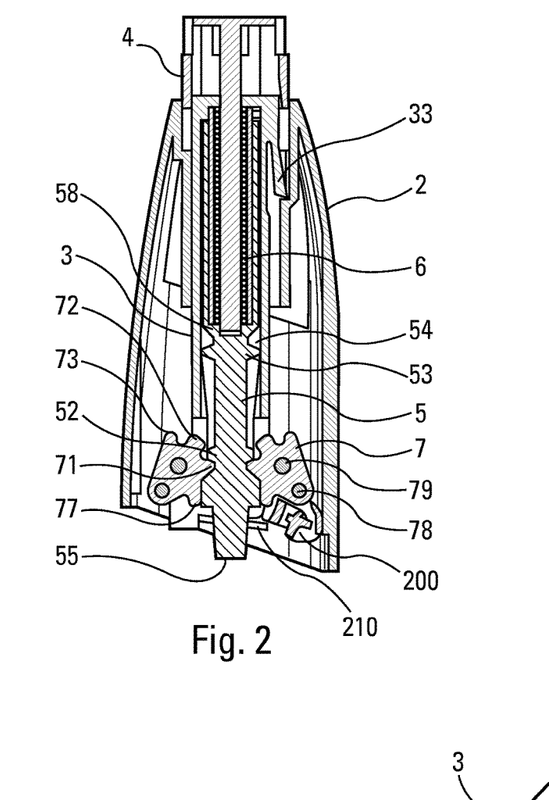
FIG. 2 is a section view of a detail of the FIG. 1 device.
Figure 3:
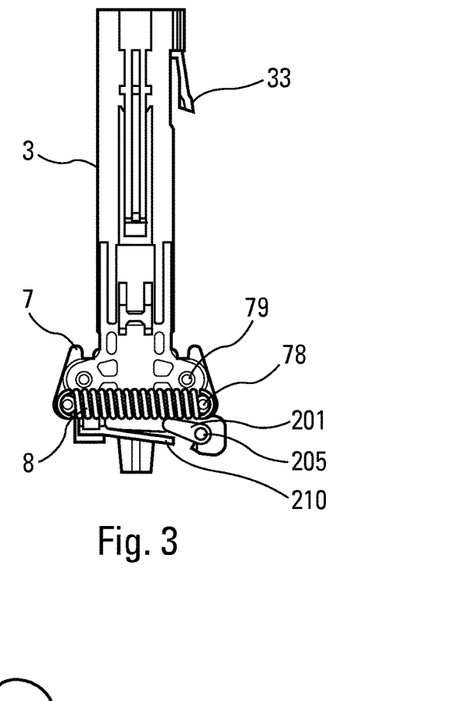
FIG. 3 is a side view of a detail of a portion of the FIG. 1 device.

With reference to FIG. 1, the various components of the autoinjector, in an advantageous first embodiment, are shown in an exploded view.

In the order of the numerical references, the autoinjector comprises a lower body 1, an upper body 2 containing a sleeve 3, an axial actuator button 4, a piston rod 5, an actuator spring 6, and two pivot members 7 that are interconnected by means of two resilient elements 8, which are preferably in the form of springs.

It should be observed that the lower and upper bodies could be replaced by a single body. Alternatively, a body constituted by more than two body portions may also be envisaged.

A reservoir S is inserted into said autoinjector, in particular into its lower body 1. The reservoir S contains fluid and includes a piston and a needle (not shown in this embodiment). The piston is adapted to move in said reservoir S so as to inject the fluid through said needle.

The present description is made with reference to a syringe S that may be of any type. More generally, it is understood that the term "syringe" in the present description encompasses any type of reservoir associated with a needle. Preferably, the reservoir S is a pre-filled syringe.

The lower body 1, at its leading end (in the travel direction of the syringe S), includes an opening through which the needle passes during the pricking stage.

The lower body 1 contains an actuator sleeve 100 having an axial end surface 105 that is in contact with the part of the user's body where injection should take place. After actuation, the actuator sleeve 100 covers the needle of the syringe S so as to avoid any risk of pricking with said needle. The actuator sleeve 100 is adapted to slide relative to said lower body 1 between an initial rest position in which it projects axially out from said lower body 1 prior to actuation, an actuated position in which it moves axially towards the inside of said lower body 1, and a final safety position in which it once again projects out from said lower body 1, so as to cover the needle of the syringe S after injection. It should be observed that the final safety position may be identical to the initial rest position, or, in a variant, the two positions may be different, e.g. with the actuator sleeve 100 axially extending out from said lower body 1 in said final safety position further than in said initial rest position. The actuator sleeve 100 is advantageously urged axially towards the outside of said lower body 1 by a spring 110.

The lower body 1 may also contain an inner body 120 that is able to receive a reservoir support element 130 into which said syringe S is inserted.

The upper body 2 is fastened to the lower body 1 and it may receive a central sleeve 3 that is adapted to house the piston rod 5 and the spring 6.

The axial actuator button 4 may be mounted to slide axially relative to the upper body 2, and in contact with the piston rod 5. Thus, by pressing on the axial button 4 so as to drive it axially into the upper body 2, the piston rod 5 is moved axially, thereby making it possible to actuate the device as described below. In a variant, the axial button could be replaced by a lateral button.

The piston rod 5 includes a trailing portion 54 and a leading end 55 in the travel direction of the piston rod 5 in the upper body 2.

In this embodiment, the trailing portion 54 defines a tubular portion that receives the spring 6 and a portion of the axial button 4.

The purpose of the leading end 55 is to contact the piston of the syringe S, so as to move said piston and thus inject the fluid contained in the syringe S through the needle.

The piston rod 5 may also include a plurality of radial projections 52, 53: a first radial projection 52, that is close to the leading end 55, and that defines a shoulder-forming leading surface 51; and a second radial projection 53, that is axially offset from said first radial projection 52 towards the trailing end 54, and that defines both a leading surface and a trailing surface. Naturally, this is only an embodiment example, and a person skilled in the art is capable of making the radial projections and shoulders in a way that is different from the way shown in the drawings. In particular, said radial projections 52, 53 are not necessarily in the leading portion of the piston rod 5, as shown in the drawings, but they could be made on another portion of the piston rod 5. Indentations could alternatively replace the projections.

The actuator spring 6 may bear firstly against the sleeve 3, and secondly against the piston rod, e.g. against a fourth shoulder 58 that is axially offset from said third shoulder 53 towards the trailing portion 54. In the embodiment shown, the fourth shoulder 58 forms a base of the above-mentioned tubular portion.

The pivot members 7 are advantageously assembled in pivotable manner on the sleeve 3, and they are advantageously identical. Preferably, they are arranged on either side of the piston rod 5. They are not movable axially relative to said lower body 1, but only in pivoting about their pivot pins 79, which are parallel. In a variant, they could be assembled in some other way, in particular on the lower body 1 or on the upper body 2.

Each pivot member 7 may include a plurality of projections 71, 72, 73: a first projection 71 that is adapted to co-operate with the leading surface (in the axial travel direction of the piston rod during actuation) of the first radial projection 52 of the piston rod 5; a second projection 72 that is adapted to co-operate with the leading surface of the second radial projection 53; and a third projection 73 that is adapted to co-operate with the trailing surface of the second radial projection 53. Naturally, other embodiments can also be envisaged, e.g. with a different number of projections. Indentations could alternatively replace the projections.

The resilient elements 8 connect the two pivot members 7 together. The principle consists in combining two stationary pivot pins, in particular the pivot pins 79 of the two pivot members 7, with two movable pins, in particular the fastener points 78 of the pivot members 7 on which the resilient elements 8 are fastened.

Figure 4:
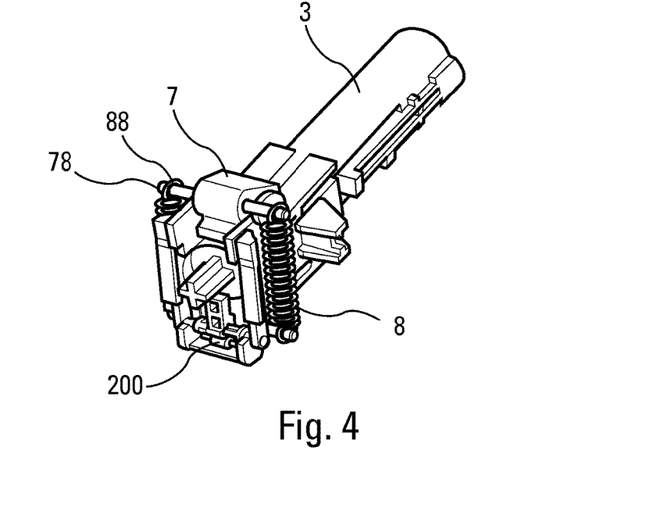
FIG. 4 is a view similar to the view in FIG. 3, as seen from below.

Thus, as can be seen in FIG. 4, the first resilient element 8 may be fastened firstly to a first fastener point of the first pivot member, and secondly to a first fastener point of the second pivot member, and the arrangement may be similar and symmetrical for the other resilient element. Preferably, each pivot member 7 includes a rod 78 having two projecting side edges. The first resilient element thus connects the first projecting edges together, and the second resilient element connects the second projecting edges together. Other variant embodiments are possible. Advantageously, when the resilient elements 8 are springs, they are identical and include eyelets 88 that are adapted to be fastened to said first and second projecting edges 78 of the pivot members 7. In a variant, the resilient elements could be different, e.g. in the form of O-rings or of other elements made of elastically-deformable material. The use of rings made of elastic material, such as O-rings, to replace the springs shown in the drawings make it possible, in particular, to reduce the amount of space the system occupies radially.

Thus, when the movable pins 78 are axially offset relative to the stationary pivot pins 79, they exert a force by means of the resilient elements 8.

When said movable pins 78 are arranged in front of said stationary pins 79 in the travel direction of the piston rod 5, the force opposes the pivoting imparted to said pivot members 7 by said piston rod 5. The pivoting of the pivot members 7 is thus braked by said resilient elements 8.

In contrast, when said movable pins 78 are arranged behind said stationary pins 79 in the travel direction of the piston rod 5, the force acts in the same direction as the pivoting imparted to said pivot members 7 by said piston rod 5. The pivoting of the pivot members 7 is thus amplified by said resilient elements 8.

When the stationary and movable pins 79, 78 are in alignment, there is a neutral point in which said resilient elements 8 do not influence the pivoting of the pivot members 7. It is in this position that the system toggles from a "braking" or "damping" state into an "amplification" state.

Such a force-adjustment system that is adapted to exert a force F1 and/or a force F2 on said piston rod 5. At the end of pricking the force F1 opposes the force exerted by the actuator spring 6 on the piston rod 5, so as to decrease the force exerted on said reservoir S by said piston rod 5 at the end of pricking. In contrast, at the beginning of injection, the force F2 is added to the force exerted by the actuator spring 6 on the piston rod 5, so as to amplify the force that is exerted on said piston P by said piston rod 5 at the beginning of injection. The force-adjustment system may exert only the force F1, only the force F2, or both of the forces F1 and F2.

FIGS. 5, 6, 7, 8, 9, 10, 11, 12, 13 and 14 show the actuation sequences of the FIG. 1 autoinjector.

Figures 5, 6, 7:
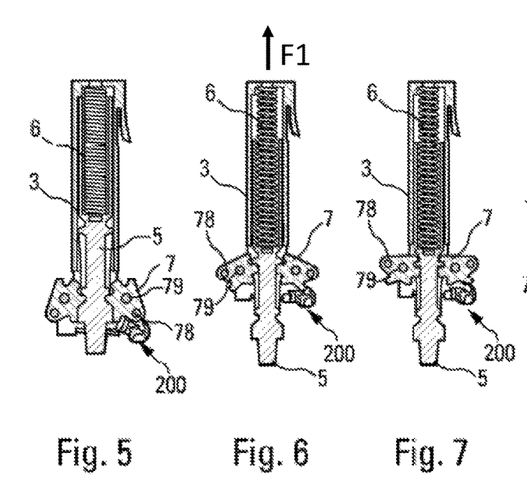
FIGS. 5, 6, 7, 8 and 9 are diagrammatic section views showing the successive sequences of the present invention, in the FIG. 1 embodiment.
Figures 10, 11:
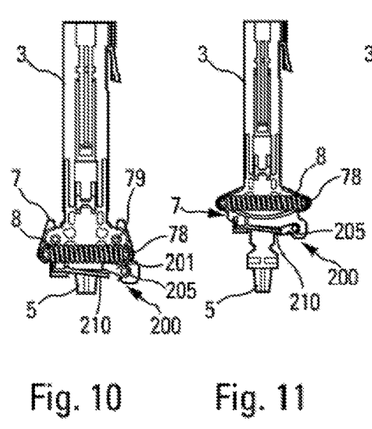
FIGS. 10, 11, 12, 13 and 14 are diagrammatic side views showing the successive sequences of FIGS. 5 to 9.

In FIGS. 5 and 10, the autoinjector is in the rest position prior to actuation. In this rest position, the needle of the syringe S is arranged inside the lower body 1. Said movable pins 78 are arranged in front of said stationary pins 79 in the travel direction of the piston rod 5. The actuator spring 6 urges the piston rod 5 towards the piston of the syringe S, but the piston rod 5 is held in the rest position by the first projection 71 of the pivot members 7 that co-operates with the first shoulder 51 of the piston rod 5. Under the pressure of the actuator spring 6, said first shoulder 51 of the piston rod 5 pushes the first projection 71 of the pivot members 7 in pivoting, but in the invention, such pivoting is prevented by a locking system 200.

More particularly, FIGS. 2, 3, 4, 15, 16, 17 and 18 show a locking system 200 in an advantageous embodiment of the present invention. The locking system 200 includes at least one locking element 201 that is movable and/or deformable between a locked position in which it prevents at least one pivot member 7 from pivoting, and an unlocked position in which said at least one pivot member 7 can pivot. In the embodiment shown, there is only a single locking element 201 co-operating with a single pivot member 7, but a locking element could be provided for each pivot member. Said locking element 201 is urged resiliently towards its locked position by a drive member 210, such as a resilient blade. Advantageously, said locking element 201 is mounted to pivot on said sleeve 3 of said body, about a pivot pin 205. In the embodiment shown, said locking element 201 comprises both a blocking portion 202 that co-operates directly with a pivot member 7, and also a control portion 203 that co-operates with an unlocking element 101 that is secured to the actuator sleeve 100. Preferably, said unlocking element 101 is formed by an axial projection of said actuator sleeve 100. The unlocking element could be made in some other way.

When the user wishes to use the autoinjector, the user takes hold of the device, e.g. at the upper body 2, and presses the actuator sleeve 100 against the part of the body where the injection is to be performed. The actuator sleeve 100 thus moves axially towards the inside of the lower body 1. When the stroke of said actuator sleeve 100 towards the inside of the lower body 1 is sufficient to enable co-operation between the locking element 201 and the unlocking element 101, the unlocking element 101 causes the locking element 201 of the locking system to pivot about its pin 205, which releases the pivot members 7. When the user relaxes the pressure on the actuator sleeve 100 without actuating the autoinjector via the actuator button 4, the resilient blade 210 returns the locking element 201 into its locked position. In particular, this enables the user to select the injection site by testing a plurality of locations without actuating the actuator button 4. When, after unlocking the pivot members 7 by pressing on the actuator sleeve 100, the user presses on the axial actuator button 4, thereby moving the piston rod 5 axially a little and causing the pivot members 7 to pivot and the autoinjector to be actuated.

Advantageously, said unlocking element 101 co-operates with said locking system 200 at the end of stroke of said actuator sleeve 100, between its initial rest position and its actuated position, in particular when said actuator sleeve 100 has performed at least 90% of said stroke. This makes it possible to stop actuating the autoinjector only when the user is certain that the fluid will be expelled at the desired injection depth, and thus avoids the risk of premature actuation at a depth that is too shallow.

As a result of the shape of the blocking portion 202 and of its position relative to the pivot pin 205 of the locking element 201 of the embodiment shown in FIGS. 15, 16, 17 and 18, if the user presses on the axial button 4 without unlocking the locking system 200, blocking is reinforced. The locking system is thus engaged, which reinforces safe actuation.

The pivoting of the pivot members 7 generated by the actuation force causes the first projection 71 and the first shoulder 51 to disengage from each other. This thus releases the piston rod 5 that is then moved axially under the effect of the actuator spring 6. This causes the syringe S to move in the lower body 1 and thus causing pricking.

When the second projection 72 of the pivot members reaches the leading surface of the second radial projection 53 of the piston rod 5, the pricking stage is not completely terminated. This can be seen in FIGS. 6 and 11. At this moment, the leading surface of the second radial projection 53 causes the pivot members 7 to pivot still further by pushing on their second projections 72. This tensions or loads the resilient elements 8 still further, which elements thus oppose an increasing force against pivoting of the pivot members 7. This generates a "braking" or "damping" force. This generates damping at the end of pricking, by decreasing the force exerted by the piston rod 5 on the syringe S, thereby greatly improving the comfort of the user and avoiding damaging the collar of the syringe S. Naturally, the forces of the actuator spring 6 and of the resilient elements 8 are selected so that pricking is only damped without being stopped.

As the pivot members 7 pivot during the pricking stage, the resilient elements 8 become increasingly tensioned. Simultaneously, the movable pins 78 of the pivot members 7 move progressively towards the stationary pins 79. The device is advantageously adjusted so as to generate maximum torque at (or just prior to) the end of the pricking stage. The neutral point in which the movable and stationary pins are in alignment may thus be reached at (or just prior to) the end of the pricking stage.

Figure 12:
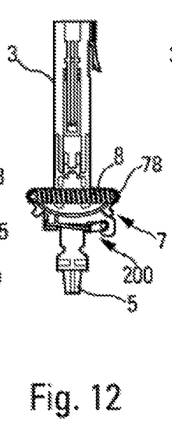

When the pivot members 7 and the resilient elements 8 are in the neutral position, shown in FIGS. 7 and 12, the piston rod is still urged axially by the actuator spring 6. Thus, the neutral position is not stable, and the system toggles automatically from the state of braking pricking to the state of amplifying the beginning of injection. Optionally, the third projection 73 may be arranged relative to the second projection 72 so that, immediately after passing the neutral position, the pivot members 7 pivot a little under the effect of the tensioned resilient elements 8. This may enable an audible sound to be generated when said third projection 73 hits the second radial projection 53 of the piston rod, so as to inform the user of the beginning of the injection stage.

Figure 8:
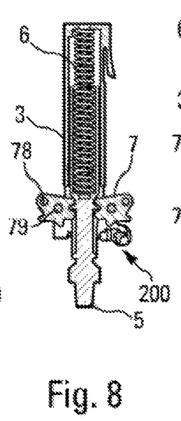
Figures 13, 14:
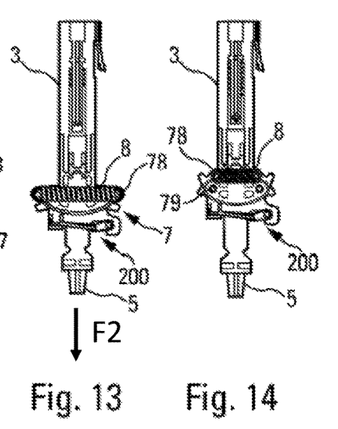
Figure 15:
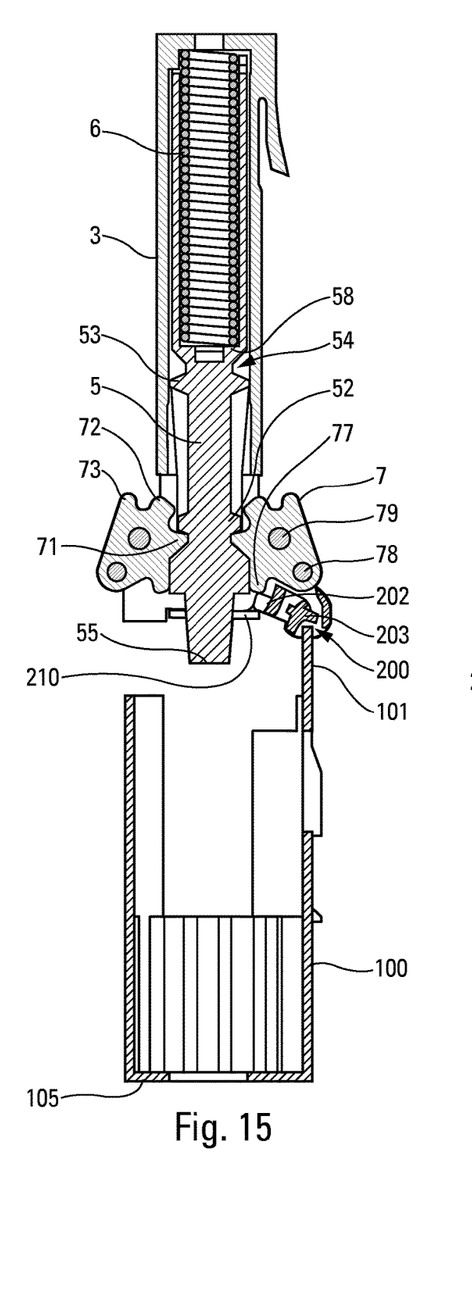
FIGS. 15, 16, 17 and 18 are diagrams showing the unlocking of the pivot members, at the beginning of actuation.
Figure 16:
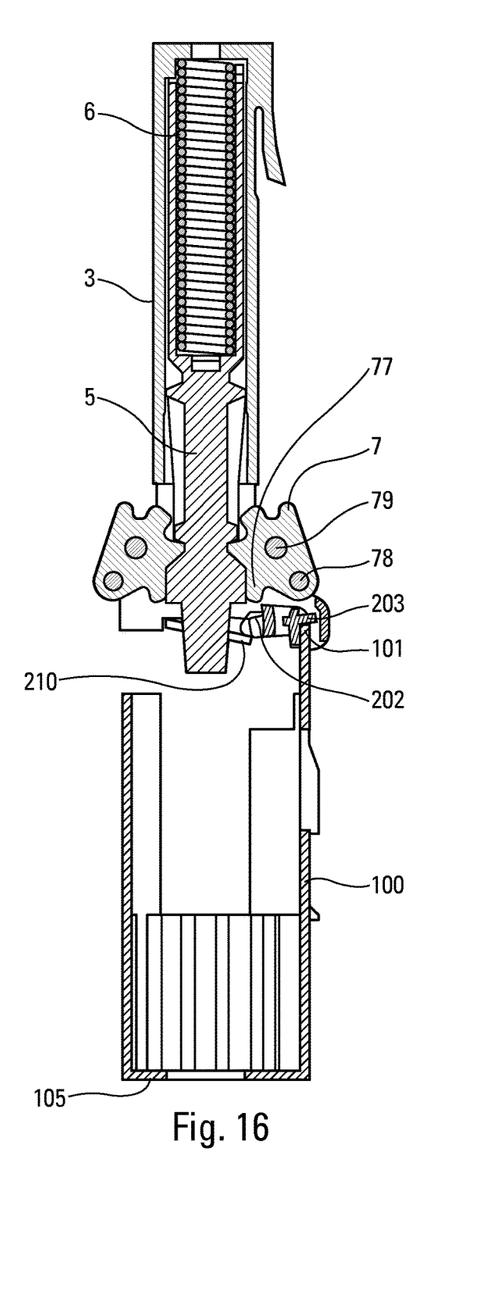
Figure 17:
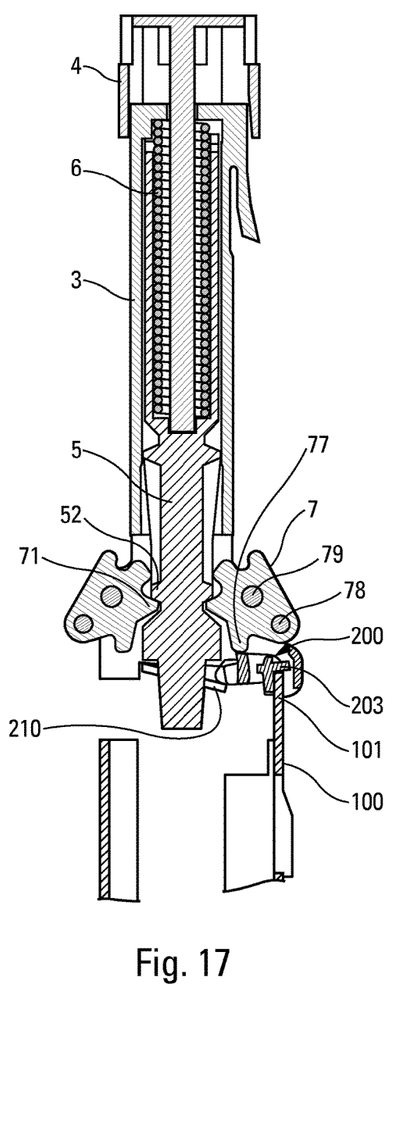
Figure 18:
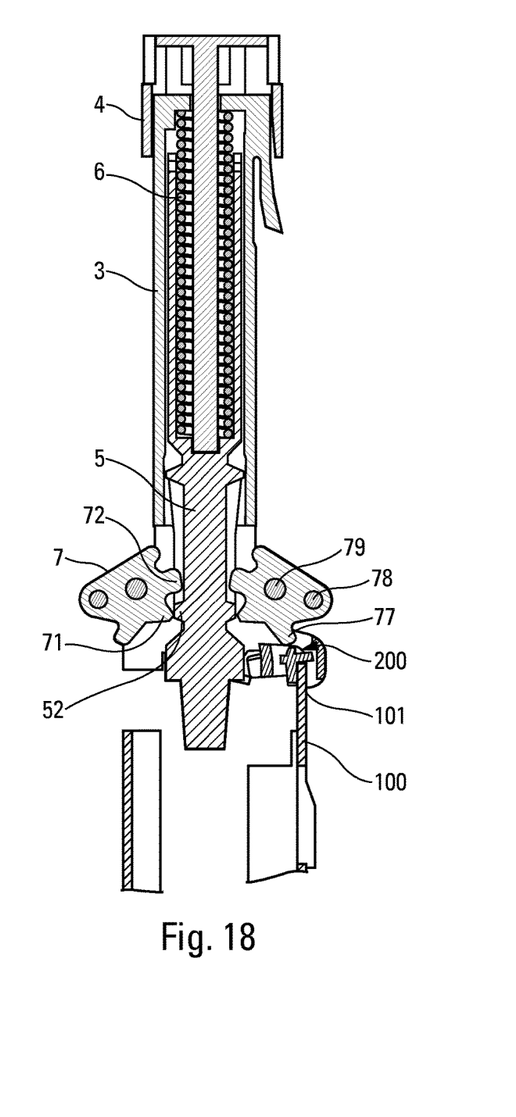

When the needle reaches its pricking position with the needle fully inserted, the injection stage is triggered, and this is shown in FIGS. 8 and 13. The leading end 55 of the piston rod then pushes on the piston under the effect of the force exerted by the actuator spring 6. During the entire injection stage, the piston rod 5 slides inside the syringe S, pushing the piston of said syringe under the effect of the spring 6. The fluid is thus dispensed through the needle.

At the beginning of the injection stage, the third projection 73 of each pivot member 7 thus comes into contact with the trailing surface of the second radial projection 53. As at the end of the pricking stage, the torque exerted by the system is at a maximum immediately after the neutral position, and the tensioned resilient elements 8 thus urge the pivot members 7 strongly in pivoting. This causes the force of the actuator spring 6 to be amplified at the beginning of the injection stage. This amplification increases the force exerted by the piston rod 5 on the piston, and thus makes it possible to guarantee that the piston starts to move from its rest position, without having to increase the force of the actuator spring 6. Specifically, the maximum resistance during the injection stage is created when starting movement of the piston. Once injection has begun, the friction of the piston in the syringe S, the viscosity of the fluid to be injected, and the resistance of the narrow passage of the needle are smaller and thus no longer require the same force from the actuator spring 6.

Figure 9:
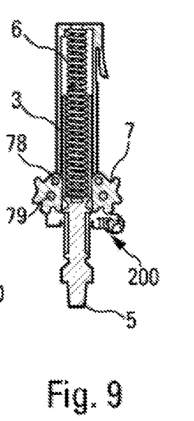

As can be seen in FIGS. 9 and 14, the pivot members 7 are disengaged from the piston rod after an injection stroke of the piston rod 5 that is relatively small, typically a few millimeters, e.g. about 4 millimeters (mm). From this disengagement, the system becomes inactive, and the injection of the fluid follows in the usual way. It may be envisaged to adapt the force-adjustment system so that it can amplify the force exerted on the piston for a greater fraction of the injection stroke, e.g. about 20 mm, or for the entire injection stroke, in particular with reservoirs having an axial dimension that is short.

FIGS. 19, 20, 21 and 22 show a second advantageous embodiment of the autoinjector in which there is no automatic pricking, or auto-pricking. It should be observed that these figures are diagrammatic only and non-limiting of such an embodiment. In this embodiment, the actuator spring 6 performs injection only, by moving the piston rod 5, and thus the piston P, between the rest position and the injection position. In this embodiment, pricking is performed manually by means of the actuator sleeve 100. In this embodiment, the syringe S is thus stationary relative to the body of the autoinjector.

Figure 19:
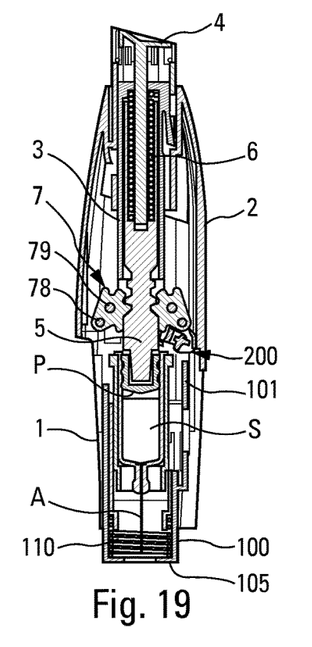
FIGS. 19, 20, 21 and 22 are section views showing another embodiment of the invention.
Figure 20:
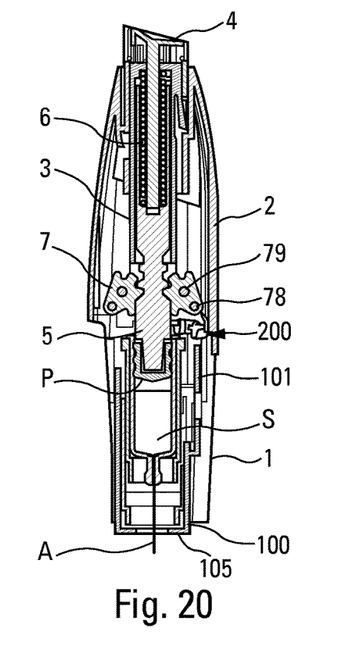
Figure 21:
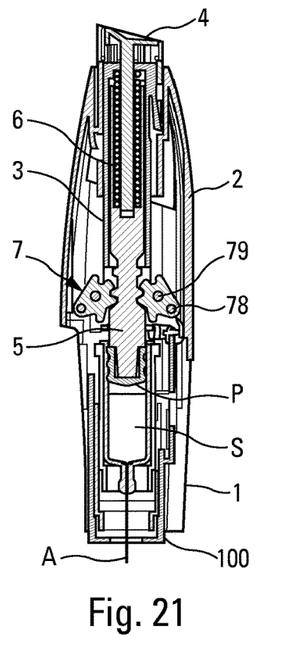
Figure 22:
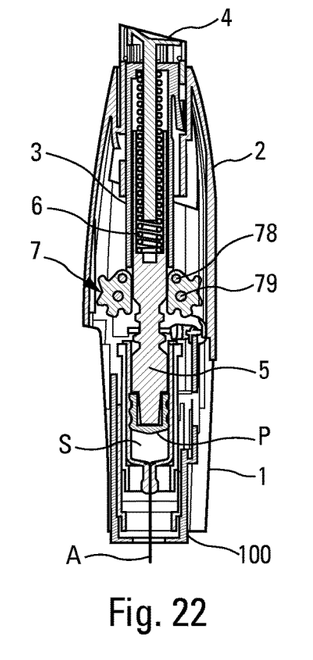

In the rest position shown in FIG. 19, the actuator sleeve 100, urged by its spring 110, surrounds the needle A of the syringe S. When the user wishes to actuate the autoinjector, the user places the axial end surface 105 of the actuator sleeve 100 against the injection site and presses on the autoinjector. The actuator sleeve 100 then slides axially towards the inside of the lower body 1, thus exposing the needle A of the syringe S that then penetrates into the body of the user, as can be seen in FIG. 20. The user may then actuate the axial button 4 so as to move the piston rod 5, and the force-adjustment system then becomes active as described above, acting via the pivot members 7 to exert an amplification force F2 on the piston rod 5 at the beginning of injection, as shown in FIG. 21. FIG. 22 shows the pivot members 7 disengaged from the piston rod 5, the end of injection thus continuing without any action from said pivot members. In a variant, it could be envisaged to cause the pivot members to act during the entire injection stage.

The locking system 200 is identical to the above-described first embodiment, and is therefore not described below.

In this embodiment, the force-adjustment system thus exerts only the amplification force F2 at the beginning of injection, and does not intervene during pricking.

Typically, it is possible to obtain damping and/or amplification forces F1, F2 of about 30 newtons (N). Naturally, other damping and braking values could be obtained by selecting in appropriate manner the resilient elements 8, and by dimensioning in appropriate manner the pivot members 7.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to two advantageous embodiments, naturally various modifications are possible for the person skilled in the art, without going beyond the ambit of the present invention, as defined by the accompanying claims.

The invention claimed is:

1. An autoinjector comprising a body (1, 2), and a reservoir (S) containing fluid and including a piston and a needle said autoinjector further comprising a piston rod (5) that is adapted to co-operate with the piston of said reservoir (S), said piston rod (5) movable between a rest position and an injection position in which said piston rod (5) has moved the piston of the reservoir (S) so as to inject the fluid through the needle, an actuator spring (6) provided so as to urge said piston rod (5) towards the injection position, the autoinjector further comprising a force-adjustment system (7, 8) that is adapted to exert at least one amplification force (F2) on said piston rod (5), said amplification force (F2) adding to a force exerted by said actuator spring (6) on said piston rod (5) at a beginning of injection, so as to amplify a force exerted on said piston by said piston rod (5) at the beginning of injection, said force-adjustment system (7, 8) comprising two pivot members (7) that co-operate with said piston rod (5), said pivot members (7) connected together by two resilient elements (8), wherein at least one pivot member (7) is blocked prior to actuation by a locking system (200), thus preventing the autoinjector from being actuated, said autoinjector further comprising an unlocking element (101) that is adapted to move and/or to deform said locking system (200) so as to unblock said at least one pivot member (7), and thus make it possible to actuate the autoinjector, wherein said body includes a sleeve, said pivot members pivotably mounted on said sleeve about stationary pivot pins (79) that are parallel;

wherein said resilient elements (8) are fastened to said pivot members via parallel moveable pins (78) that are formed on said pivot members (7); and wherein, when the piston rod moves towards the injection position, said moveable pins (78) are arranged behind said stationary pivot pins (79) in a travel direction of said piston rod and said resilient elements, at a beginning of travel of the piston rod towards the injection position, are loaded causing said pivot members to pivot in such a manner as to relax said resilient elements, thereby creating the amplification force (F2) at the beginning of injection.

2. An autoinjector according to claim 1, wherein each pivot member (7) includes a plurality of projections (71, 72, 73) that are arranged to co-operate with a plurality of radial projections (52, 53) of the piston rod (5).

3. An autoinjector according to claim 1, wherein said autoinjector is actuated by an axial button (4).

4. An autoinjector according to claim 1, wherein, prior to injection, said piston rod (5) is initially moved by said actuator spring (6) between said rest position and a pricking position in which said piston rod (5) has moved said reservoir (S) relative to said body (1, 2) so as to perform pricking.

5. An autoinjector according to claim 4, wherein, during pricking, the piston rod (5) co-operates with the piston of the reservoir (S) so as to move said reservoir (S) relative to the body (1, 2).

6. An autoinjector according to claim 1, wherein, when the piston rod (5) moves from the rest position towards a pricking position, said movable pins (78) are arranged in front of said stationary pivot pins (79) in the travel direction of said piston rod (5), said piston rod (5), at the end of travel towards the pricking position, causing said pivot members (7) to pivot so as to load said resilient elements (8), thereby creating a braking force (F1) at an end of pricking, said braking force (F1) being opposed, at the end of pricking, to the force exerted by said actuator spring (6) on said piston rod (5), so as to decrease a force exerted on said reservoir (S) by said piston rod (5) at the end of pricking.

7. An autoinjector according to claim 1, wherein, said locking system (200) includes at least one locking element (201) that is movable and/or deformable between a locked position which prevents at least one pivot member (7) from pivoting, and an unlocked position in which said at least one pivot member (7) can pivot.

8. An autoinjector according to claim 7, wherein, said at least one locking element (201) is urged resiliently towards the locked position by a drive member (210).

9. An autoinjector according to claim 7, wherein, said at least one locking element (201) is pivotably mounted on a sleeve (3) of said body (1,2), about a pivot pin (205).

10. An autoinjector according to claim 7, wherein said at least one locking element (201) includes a blocking portion (202) that co-operates directly with a pivot member (7), and a control portion (203) that co-operates with said unlocking element (101).

11. An autoinjector according to claim 1, wherein said unlocking element (101) is formed on an actuator sleeve (100) that is slidably mounted in said body (1, 2), and that has an axial end surface (105) that is in contact with the zone in which injection is to take place, said actuator sleeve (100) adapted to slide relative to a lower part of the body (1) between an initial rest position in which the actuator sleeve projects axially out from the lower part of the body (1) prior to actuation, an actuated position in which the actuator sleeve is moved axially towards an inside of the lower part of the body (1), and a final safety position in which the actuator sleeve once again projects out from the lower part of the body (1), so as to cover the needle of the syringe (S) after injection, said actuator sleeve (100) being urged axially towards the outside of the lower part of the lower body (1) by a spring (110).

12. An autoinjector according to claim 11, wherein said unlocking element (101) co-operates with said locking system (200) at the end of stroke of said actuator sleeve (100), between the initial rest position and the actuated position, in particular when said actuator sleeve (100) has performed at least 90% of said stroke.

13. The autoinjector according to claim 1, wherein the piston and needle form a part of a pre-filled syringe.

14. The autoinjector according to claim 1, wherein the parallel movable pins are rods having two side edges.

15. The autoinjector according to claim 8, wherein the drive member is a resilient blade.

\* \* \* \* \*